(12) United States Patent  (10) Patent No.: US 8,591,448 B2
Powers et al.  (45) Date of Patent: Nov. 26, 2013

(54) PRESSURE MONITORING WITHIN A FLUID CASSETTE (75) Inventors: Edward T. Powers, Hampton Falls, NH (US); Matthew J. Murphy, Braintree, MA (US); Michael Ragusa, Hingham, MA (US)

(73) Assignee: Haemonetics Corporation, Braintree, MA (US)

( * ) Notice: Subject to any disclaimer, the term of this patent is extended or adjusted under 35 U.S.C. 154(b) by 493 days.

(21) Appl. No.: 12/465,327

(22) Filed: May 13, 2009

(65) Prior Publication Data

US 2010/0292628 A1 Nov. 18, 2010

(51) Int. Cl.
*A61M 37/00* (2006.01)
*C02F 1/44* (2006.01)

(52) U.S. Cl.
USPC ............ 604/4.01; 604/6.11; 210/741; 210/90

(58) Field of Classification Search
USPC .............. 604/4.01, 5.01, 6.01, 6.11; 210/645, 210/252, 90, 741; 417/477.2
See application file for complete search history.

(56) References Cited

U.S. PATENT DOCUMENTS

| | | | | |
|---|---|---|---|---|
| 4,804,360 A | 2/1989 | Kamen | ......................... | 604/250 |
| 5,273,517 A | 12/1993 | Barone et al. | ................... | 494/37 |
| 5,311,908 A | 5/1994 | Barone et al. | ................... | 137/881 |
| 5,795,317 A | 8/1998 | Brierton et al. | ................... | 604/5 |
| 6,074,359 A * | 6/2000 | Keshaviah et al. | ............. | 604/29 |
| 6,117,086 A | 9/2000 | Shulze | ........................ | 600/488 |
| 6,280,406 B1 | 8/2001 | Dolecek et al. | .............. | 604/4.01 |
| 6,409,696 B1 * | 6/2002 | Toavs et al. | ................... | 604/6.01 |
| 6,684,710 B2 * | 2/2004 | Chevallet et al. | .............. | 73/723 |
| 6,755,801 B2 | 6/2004 | Utterberg et al. | ............ | 604/4.01 |
| 7,169,352 B1 | 1/2007 | Felt et al. | ........................ | 422/44 |
| 2001/0048892 A1 | 12/2001 | Bainbridge et al. | ............ | 422/44 |
| 2007/0179433 A1 * | 8/2007 | Jonsson et al. | .................. | 604/31 |
| 2007/0232980 A1 | 10/2007 | Felt et al. | ....................... | 604/6.1 |

FOREIGN PATENT DOCUMENTS

| | | | | |
|---|---|---|---|---|
| EP | 1 813 300 | 8/2007 | ............ | A61M 5/145 |
| WO | WO 99/13926 | 3/1999 | .............. | A61M 1/36 |
| WO | WO 00/23140 | 4/2000 | ............ | A01M 37/00 |

OTHER PUBLICATIONS

European Patent Office, International Search Report and the Written Opinion of the International Searching Authority—International Application No. PCT/US2010/034374, dated Aug. 16, 2010 (13 pages).

* cited by examiner

*Primary Examiner* — Leslie Deak
(74) *Attorney, Agent, or Firm* — Sunstein Kann Murphy & Timbers LLP (57) ABSTRACT

A fluid cassette for a blood processing system includes a cassette housing and a rigid structure. The cassette housing defines the structure of the cassette and has a fluid path at least partially extending through it. The fluid path is configured to allow a fluid to pass through the housing. The rigid structure defines a cavity that is in fluid communication with the fluid path. The rigid structure also has an interface for interfacing and/or connecting with a pressure monitoring device. The interface allows the pressure monitoring device to measure the pressure within the fluid path. The cavity has a volume of air located between the fluid path and the interface.

41 Claims, 6 Drawing Sheets

PRESSURE MONITORING WITHIN A FLUID CASSETTE

TECHNICAL FIELD

The present invention relates to blood processing devices, and more particularly to pressure monitoring within cassette-based blood processing devices.

BACKGROUND ART

Many current blood systems process a number of fluids and have complex fluid path arrangements and they often use one or more cassettes to organize the lines and fluid paths. The cassettes organize the fluid lines, allow for a smaller overall system, and greatly simplify device loading and setup. An example of blood processing is apheresis. Apheresis is the process of removing whole blood from a patient or donor, separating the blood into its various components, removing one or more of the components, and returning the remaining components to the patient.

During blood processing, the pressure within the fluid lines is critical to patient safety and system performance and efficiency. That that end, blood processing systems typically monitor the pressure within some or all of the fluid lines (especially the draw and return lines). In an apheresis device, for example, the donor pressure may be monitored to ensure that it does not go above or below a threshold during withdrawal of whole blood and return of blood components. A few solutions to pressure monitoring have been implemented but each has significant drawbacks.

Some prior art systems have a monitoring line connected to the fluid line. The monitoring line may contain a 0.2 micron filter and may be manually connected to a pressure transducer by way of a tapered luer fitting. As the pressure within the fluid line increases, the fluid compresses a column of air trapped in the monitoring line between the flowing fluid and the transducer. The pressure transducer then detects the change in pressure. The system can detect a drop in pressure in a similar manner. Although this approach has been proven effective, it has several drawbacks. First, such designs may not easily be incorporated into a cassette. Additionally, these designs require the operator to connect to each transducer manually, making it prone to bad connections. If the connection is not air-tight, fluid may force the air out of the column and wet the transducer protector. If this happens, the sensor/transducer will no longer function.

Other prior art systems have taken a different approach. These systems have a flexible membrane (silicone, for example) within the fluid path. The membrane is in contact with the fluid on one side and a transducer on the other. Increases in pressure within the fluid line create a pressure on the transducer through the flexible membrane. However, these systems will not detect a negative pressure without the presence of a metallic disk attached to the transducer side of the membrane. The systems may then use a magnet, incorporated into the membrane, to create a coupling to the membrane even during negative pressure. This approach also has been proven effective but has a significant disadvantage in cost and complexity. Both the membrane and metallic disk add cost to the set and add complexity to the manufacturing and set-up process.

SUMMARY OF THE INVENTION

In a first embodiment of the invention there is provided a fluid cassette for a blood processing system. The cassette may include a cassette housing and a rigid structure (e.g., a dome or a pathway). The cassette housing defines the structure of the cassette and has a fluid path at least partially extending through the housing. The fluid path allows fluids to pass through the housing. The rigid structure defines a cavity that is in fluid communication with the fluid path, and has an interface that mates/interfaces with a pressure monitoring device. The pressure monitoring device may measure the pressure within the fluid path. The cavity has a volume of air located between the fluid path and the interface.

The fluid cassette may also have a bacteriostatic filter located within the rigid structure. For example, the filter may be located at the top of the rigid structure and pass through the interface. The filter may ensure that the fluid path remains sterile and the volume of air may prevent fluid within the fluid path from contacting the bacteriostatic filter. The filter may be a porous plastic plug and may be hydrophobic.

The volume of air within the cavity may translate changes of pressure within the fluid path to the pressure monitoring device by compressing and expanding in response to increases and decreases in the pressure within the fluid path. For example, an increase in pressure within the fluid path may compress the volume of air, thereby increasing the pressure on the pressure monitoring device. The volume of air may be large enough so that, when the volume of air is fully compressed, the volume of air prevents the fluid within the fluid path from contacting the bacteriostatic filter.

In accordance with related embodiments, the cassette may also have a vertical standpipe located within the cavity of the rigid structure. The bacteriostatic filter may be located at the bottom of the standpipe. The standpipe may have a standpipe volume that is not included in the internal volume of air. In embodiments where the rigid structure is a pathway, the pathway may include a fluid connection pathway and an internal volume pathway. The fluid connection pathway may provide fluid communication between the fluid path and the internal volume pathway. The interface and the filter may be located within the internal volume pathway In accordance with additional embodiments of the present invention, a method for monitoring pressure within a fluid cassette for a blood processing system includes inserting a fluid cassette into the blood processing system, initiating blood processing, and measuring the pressure within a fluid path in the cassette. As the operator/technician inserts the fluid cassette, a pressure monitoring device connects to an interface located on/within a rigid structure. The rigid structure defines a cavity in fluid communication with the fluid path located within the fluid cassette. The cavity has a volume of air located between the fluid path and the interface. The measured pressure within the fluid path may be a function of the amount of compression of the volume of air within the cavity.

The fluid cassette may include a bacteriostatic filter that ensures the fluid path remains sterile. The filter may be located at the top of the rigid structure and may pass through the interface. The volume of air within the cavity may prevent the fluid within the fluid path from contacting the bacteriostatic filter. Additionally, the volume of air within the cavity may translate changes of pressure within the fluid path to the pressure monitoring device. For example, an increase in pressure within the fluid path may compress the volume of air, which, in turn, increases the pressure measured by the pressure monitoring device. The volume of air may be large enough such that when it is fully compressed, it prevents fluid within the fluid path from contacting the bacteriostatic filter.

In accordance with still further embodiments of the present invention, a pressure monitoring system for use in an apheresis device includes a fluid cassette, a base unit that mates with the fluid cassette, and a pressure monitoring device. The fluid cassette may have a rigid structure and a fluid path through it that allows fluid to pass through the cassette. The rigid structure may have a cavity that is in fluid communication with the fluid path. The cavity may have a volume of air located between the fluid path and the interface. The pressure monitoring device may be connectable to an interface on the rigid structure. The pressure monitoring device can measure the pressure within the fluid path, for example, based, at least in part, upon the amount of compression of the volume of air.

The pressure monitoring system may also have a bacteriostatic filter located within the rigid structure and passing through the interface. The bacteriostatic filter may ensure that the fluid path remains sterile. Additionally, the volume of air may be large enough such that when it is fully compressed, the volume of air prevents the fluid within the fluid path from contacting the bacteriostatic filter.

In accordance with other embodiments, the rigid structure may include a vertical standpipe, and the bacteriostatic filter may be located at the bottom of the vertical standpipe. The vertical standpipe may have a standpipe volume that is not included in the volume of air. The rigid structure may be a dome or a pathway. The pathway may include a fluid connection pathway and an internal volume pathway. The fluid connection pathway provides fluid communication between the fluid path and the internal volume pathway, and the interface may be located within the internal volume pathway.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

In illustrative embodiments, a fluid cassette 100 for a blood processing system has improved pressure monitoring capabilities. As discussed above, blood processing systems, such as apheresis systems, utilize fluid cassettes to organize and simplify the fluid flow through the system. In general, apheresis systems withdraw whole blood from a donor, separate the whole blood into its components, remove and/or collect certain components (e.g., red blood cells, platelets, plasma, etc.), and return the remaining components to the donor. During both the draw and return processes, the blood apheresis system must monitor pressures within the fluid lines and cassette 100 to ensure the pressures are neither too high nor too low. Doing so avoids potential injury to the donor and helps optimize system efficiency and performance. Embodiments of the fluid cassette 100 may be used in a variety of fluid/blood apheresis systems to improve and simplify the pressure monitoring capabilities of the system.

Figure 1:
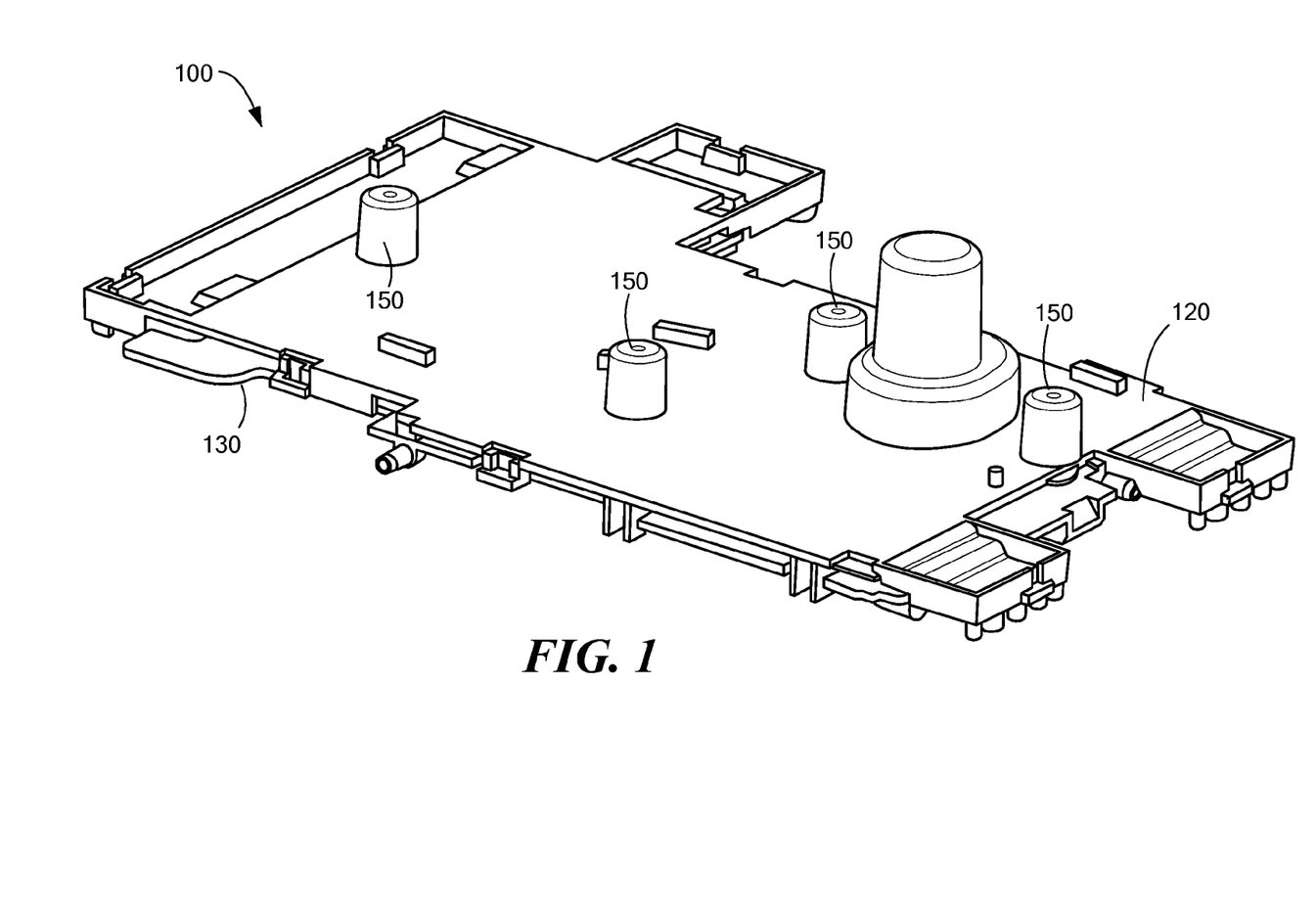
FIG. 1 schematically shows a perspective view of a fluid cassette configured in accordance with one embodiment of the present invention.

FIG. 1 schematically shows a blood cassette 100 in accordance with embodiments of the present invention. The blood cassette 100 has a housing 110 that defines the structure of the cassette 100. The housing may be a single piece or a multi-piece structure. For example, the housing may have a top housing 120 and a bottom housing 130. The housing components can be assembled in a variety of ways including, but not limited to, snap-fit, ultrasonic welding, and plastic welding. Regardless of the number of housing components and the method of assembly, the housing 110 should be sized and shaped appropriately to allow the cassette 100 to easily mate with the blood apheresis system.

The housing 110 may include a number of fluid paths 210 (FIG. 2) passing though the cassette 100. For example, the housing may have a withdrawal fluid path and a return fluid path. The inlet of the withdrawal flow path may be connected to tubing leading to the patient/donor. Blood withdrawn from the patient/donor may enter the fluid cassette 100 through the withdrawal flow path inlet, flow through the withdrawal flow path and out the withdrawal flow path outlet. The withdrawal flow path outlet may lead to additional blood processing equipment (not shown) such as centrifuges, pumps, blood cleaning devices, or other equipment that can be used to separate the blood into its components or otherwise process the withdrawn blood. In a similar manner, the return flow path may be connected to fluid storage bags containing blood components and other fluids to be returned to the donor and/or the other blood processing equipment mentioned above. The fluids to be returned to the donor may pass through the return fluid path and cassette 100 as they are being returned to the donor. In addition to the withdrawal and return fluid paths, the cassette 100 may also have a variety of other fluid paths including, but not limited to, transfer fluid paths that connect various components of the blood apheresis system and allow fluids being transferred between the components to pass through the cassette 100.

As discussed above, the fluid cassette 100 mates with a base unit 340 (FIG. 3) during assembly. The base unit 340 may include a variety of detection and measurement devices. For example, the base unit 340 may include an air detection device that detects air bubbles within the fluid paths 210. Additionally or alternatively, the base unit 340 may include pressure monitoring devices and seals that allow the base unit/apheresis system to measure the pressures within the fluid paths 210.

Figure 2:
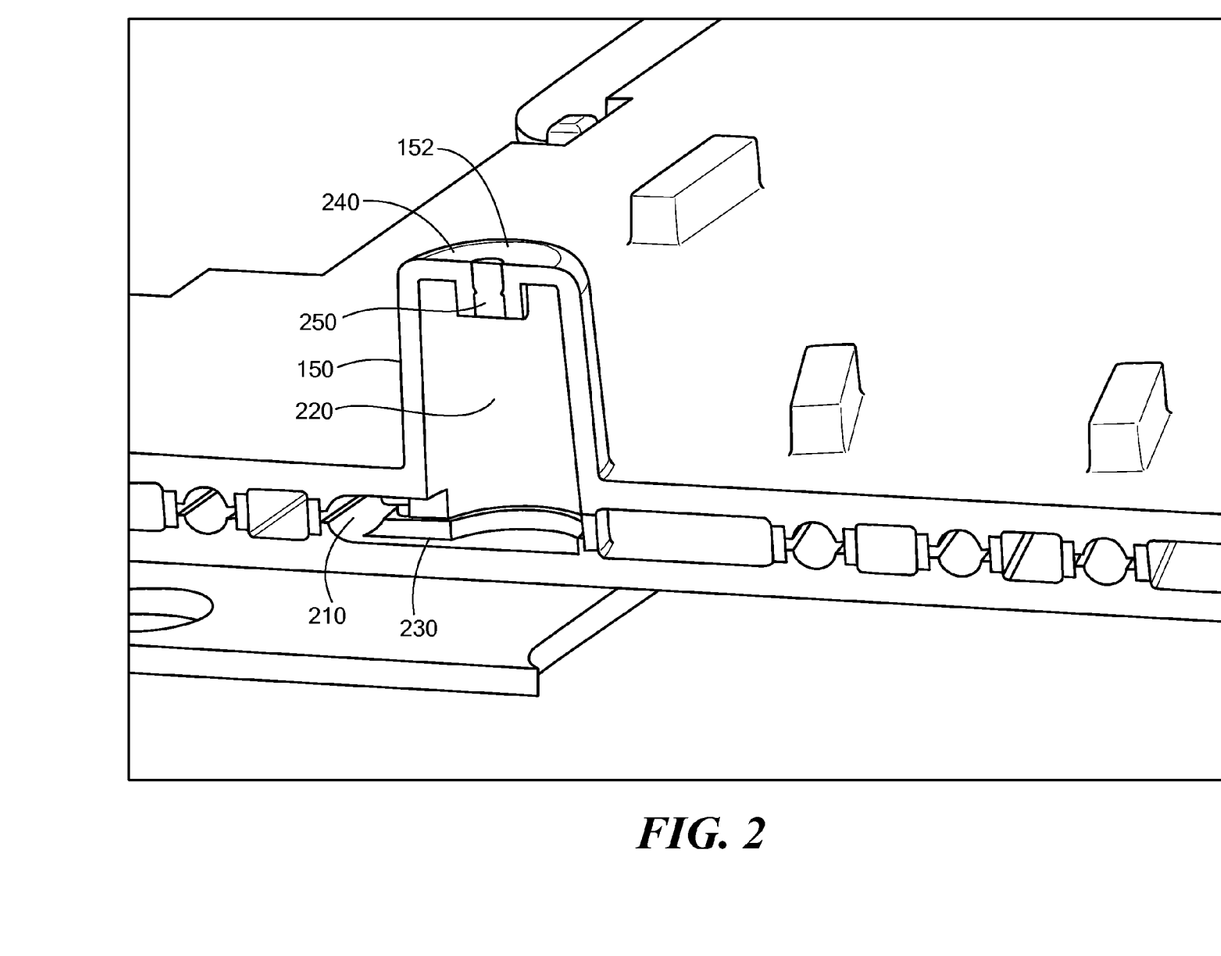
FIG. 2 schematically shows a cross-sectional view of a portion of the fluid cassette shown in FIG. 1, in accordance with embodiments of the present invention.
Figure 3:
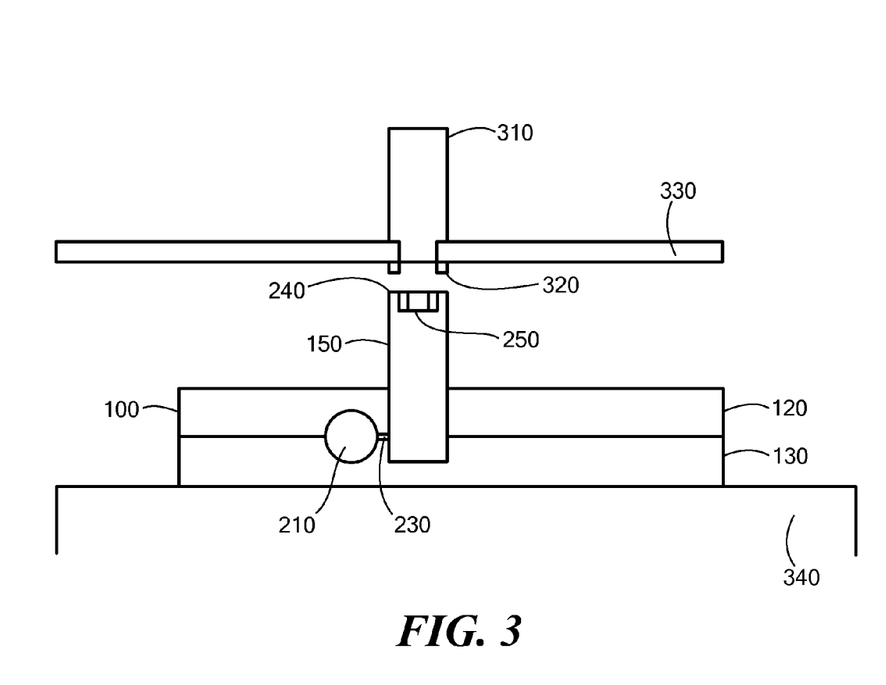
FIG. 3 schematically shows a cross-sectional view of the fluid cassette shown in FIG. 1 being inserted into a blood processing system, in accordance with embodiments of the present invention.

In order to facilitate the monitoring of pressure within the fluid paths 210, the fluid cassette 100 may have one or more rigid structures located on the housing 110. For example, as shown in FIGS. 1 and 2, the housing 110 may include a variety of pressure domes 150. As shown in FIG. 2, the pressure domes 150 may be hollow such that the interior of the pressure dome 150 is a cavity 220, which creates an internal volume of air within the pressure dome 150. The pressure dome 150, cavity 220, and thus the internal volume of air may be in fluid communication with the fluid path 210 via a fluid connection channel 230. As will be described in greater detail below, the fluid connection channel 230 and the cavity/internal volume of air 220 cooperate to translate the pressure and pressure changes within the fluid path 210 to the pressure monitoring device 310 (FIG. 3).

In addition to the cavity 220 and internal volume of air, the pressure domes 150 may also have an interface 240 at which the pressure monitoring device 310 connects to the pressure dome 150. In order to keep the fluid path 210 sterile and avoid any bacteria or other debris from entering the cavity 220 or the fluid path 210, a filter 250 may be incorporated into the top 152 of the pressure dome 150 (e.g., at the interface 240). The filter 250 may be a bacteriostatic filter and may be hydrophobic. For example, the filter 250 may be a porous plastic plug with a sufficiently torturous path through it such that the filter 250 provides a sterile barrier equivalent to a 0.2 micron filter. Alternatively, the filter 250 may be a traditional bacteriostatic filter media and may be welded in place or mechanically held in place by another suitable means. Regardless of the type or structure of the filter 250, the filter 250 must allow sufficient air flow through the filter 250 to ensure accurate pressure sensing.

In operation, as the fluid is passing through the fluid path 210, the pressure within the fluid path 210 is translated to the pressure monitoring device 310 via the fluid connection channel 230 and the internal volume of air within the cavity 220. In particular, fluid and/or pressure within the fluid path 210 will compress the internal volume of air within the cavity 220 and the pressure monitoring device 310 will then measure the pressure within the fluid path 210 based upon the amount of compression of the internal volume of air. If the pressure within the fluid path 210 increases, the fluid/pressure will compress the internal volume of air and the pressure monitoring device 310 will detect and measure the increase in pressure. Conversely, if the pressure within the fluid path 210 decreases, the internal volume of air will expand (e.g., it will become less compressed), and the pressure monitoring device 310 will detect and measure the decreased pressure.

It is important to note that the internal volume of air must be sufficiently large such that, when the internal volume of air is fully compressed, sufficient air volume remains in the cavity 220 to prevent the fluid within the fluid path 210 from contacting the filter 250. In other words, the internal volume of air must act as a buffer between the fluid and the filter 250, even when the air is maximally compressed. Accordingly, the correct amount of the internal volume of air may be a function of the maximum expected pressure within the fluid path 210, the total air volume within the pressure monitoring device 310 between the seal 320 and the pressure transducer within the pressure monitoring device 310, and the maximum expected ambient atmospheric pressure. The sum of the air volume within the instrument and the air volume within the cavity define the total closed air volume (e.g., the air volume that is compressed by the fluid within the flow path 210) of the pressure sensing system.

Additionally, it is also of note that, as the internal volume of air is compressed by the pressure of the fluid within the fluid path 210, the ideal gas law (e.g., PV=nRT) shows that the pressure and the volume are inversely proportional and the relationship between the two is linear (e.g., $P_1V_1 = P_2V_2$). In other words, if the system is required to run at an altitude as high as 8000 feet, it will be exposed to an ambient atmospheric pressure of 565 mmHg. Therefore, when the cassette 100 is loaded into the apheresis system, the internal air volume of the cavity 220 may be defined as $V_1$ and the pressure, $P_1$, is the ambient atmospheric pressure. When the flow path 210 is pressurized, that pressure (e.g., $P_2$) is a differential pressure from the ambient. Therefore, if a maximum fluid pressure within the fluid path 210 is 500 mmHg, the actual pressure on the internal air volume in the cavity 220 and pressure monitoring device 310 will be 1065 mmHg. Since $V_1$ is known, $V_2$ may be calculated. In this example, $V_2$ would be 47% less than $V_1$.

As mentioned above, the internal volume of air should have sufficient air volume in the cavity 220 to prevent the filter 250 from coming in contact with fluid. In the example provided above, the entire volume is roughly halved. Therefore, if the ratio of volume in the cavity 220 to volume in the instrument is 1:1, the cavity 220 would be filled when fully pressurized. If this were the case, the filter 250 would come in contact with fluid. Accordingly, the internal air volume within the cavity 220 should be increased. If the ratio of air volume in the cavity 220 to volume in the instrument is 2:1, then the cavity 220 will only be 75% full when fully pressurized. The exact ratio chosen depends on the safety factor required. Additionally, the overall air volume should be minimized to prevent delays in sensing pressure changes.

As mentioned above, the pressure monitoring device 310 and the corresponding seal 320 may be part of the apheresis device. In particular, as shown in FIG. 3, the pressure monitoring device 310 and the seal 320 may be located on a moving door 330. The moving door 330 may be opened in order to insert the cassette 100 and mate the cassette 100 with the base unit 340. Once the cassette 100 is in place, the moving door 330 may be closed. The seal 320 and the pressure monitoring device 310 may be located on the door 330 such that, as the door 330 is closed, the seal 320 and pressure monitoring device 310 align and seal against the interface 240. The seal can be any number of structures including, but not limited to, an o-ring.

Figure 4:
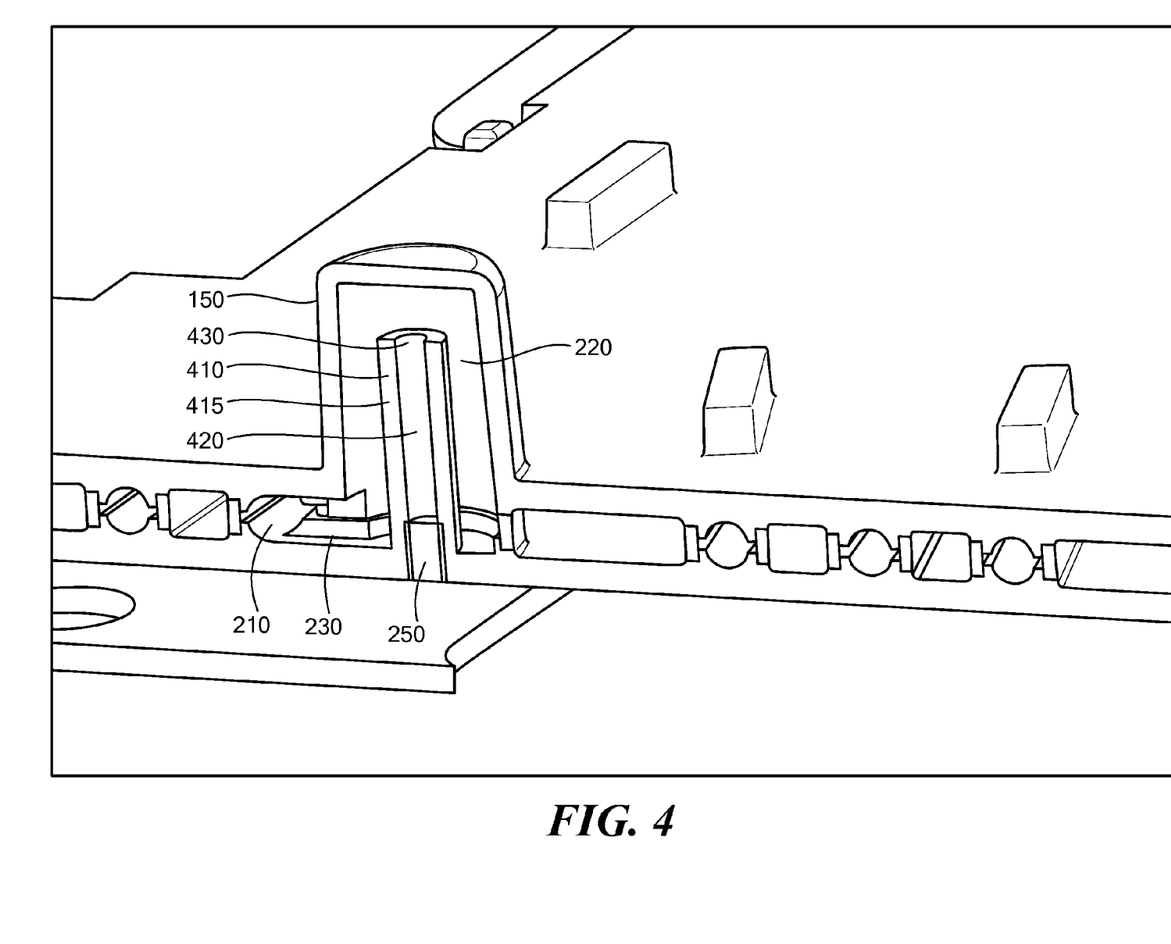
FIG. 4 schematically shows a cross-sectional view of an alternative embodiment of a fluid cassette, in accordance with embodiments of the present invention.

In accordance with other embodiments, and as shown in FIG. 4, the cassette 100 may include a standpipe 410 located within the cavity 220 of the pressure dome 150. In such embodiments, the filter 250 and the interface 240 may be located at the bottom of the standpipe 410, and thus the bottom of the cassette 100. By moving the filter 250 and interface 240 to the bottom of the cassette 100, the pressure monitoring device 310 and the seal 320 may be located below the cassette 100. In other words, the pressure monitoring device 310 and the seal 320 may be moved off of the moving door 330 and placed within the base unit 340 below the cassette 100. Therefore, as the cassette 100 is mated with the base unit 340, the connection/seal between the pressure monitoring device 310 and the interface 240 are made upon insertion of the cassette 100 (e.g., the door 330 does not need to be closed to create the connection/seal).

It should be noted that, in order to prevent the fluid from contacting the filter 250 in embodiments having the standpipe 410, the internal air volume within the cavity 220 must be sufficiently large such that fluid does not flow over the wall 415 of the standpipe 410. Accordingly, in preferred embodiments, the volume 420 within the standpipe (e.g., the standpipe volume) is not included in the calculation of the required internal volume of air within the cavity 220. Therefore, embodiments having standpipes 410 may require a somewhat larger internal volume of air within the cavity 220.

The presence of the standpipe 410 also allows the cassette 100 to be mounted in non-horizontal positions within the base unit 340. In particular, because the standpipe 410 provides an additional obstacle for the fluid to reach the filter 250, the cassette 100 may be mounted non-horizontally. However, in order to mount the cassette 100 non-horizontally, the end 430 of the standpipe 410 must be in air (e.g., no fluid from the flow path 210 may be surrounding the end 430) when the cavity 220 is fully pressurized and/or the internal volume of air is fully compressed.

Figure 5A:
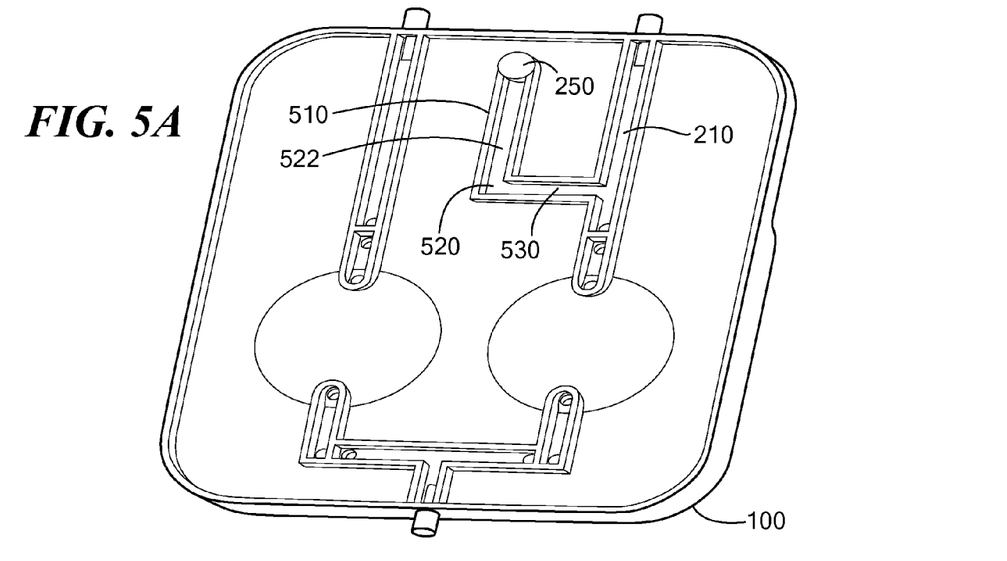
FIGS. 5A and 5B schematically show perspective views of a third embodiment of a fluid cassette in accordance with embodiments of the present invention.
Figure 5B:
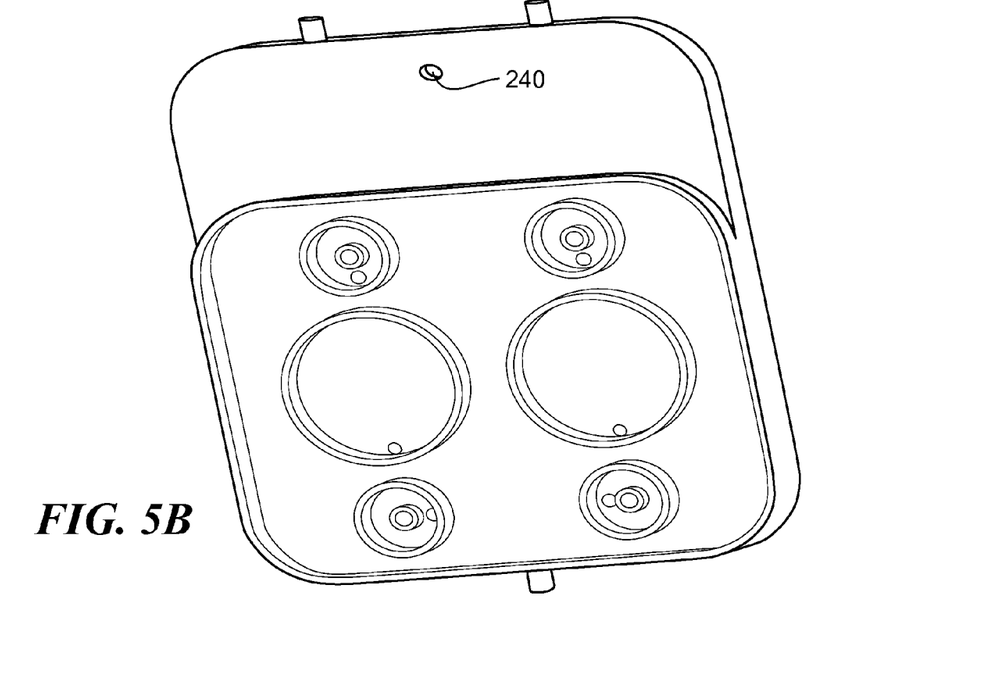

Although the internal volume of air is described above as being contained within pressure domes 150, other structures may be used to define the cavity and internal volume of air. In particular, as shown in FIGS. 5A and 5B, the cassette 100 may have a rigid structure that is a pathway 510. The pathway 510 may have an internal volume pathway 520 and a fluid connection pathway 530. In a similar manner to the pressure domes 150, the internal volume pathway 520 has a cavity 522 that creates the internal volume of air. The fluid connection pathway 530 fluidly connects the internal volume pathway 520 to the fluid path 210.

In operation, the pathway 510 works in much the same manner as the pressure domes 150 described above. In particular, the pressure within the fluid path 210 compresses the internal volume of air within the internal volume pathway 520 (e.g., via the fluid connection pathway 530). The pressure monitoring device 310 interfaced with the cassette 100 at the interface 240 may then detect and measure the compression, and, therefore, the pressure. In a manner similar to the previous embodiments, the pathway 510 may include a filter 250 located within the internal volume pathway 520 at the interface 240.

It is important to note that the pathway 510 does not need to be a raised structure like the pressure domes 150 described above. Rather, as shown in FIG. 5A, the pathway 510 may simply be an additional pathway extending off of the fluid path 210. In other words, the pathway 510 may be substantially flush with the fluid path 210. Embodiments having the pathway 510 are particularly useful in apheresis system which require a vertical cassette orientation.

Figure 6:
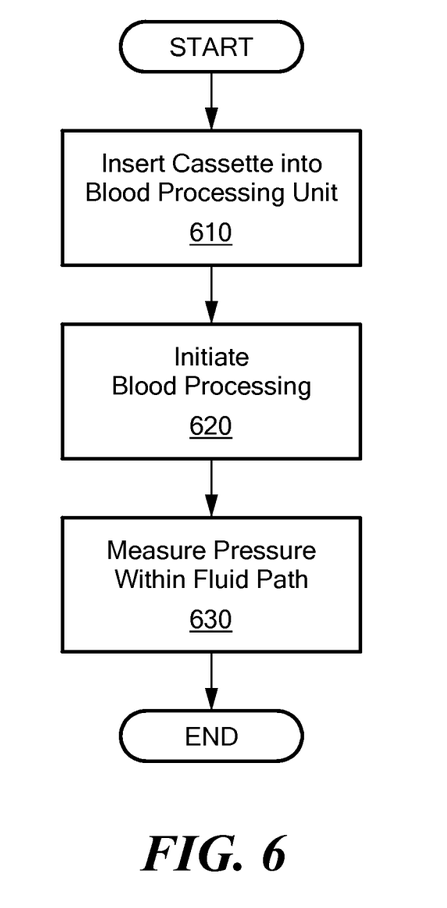
FIG. 6 shows a process of using embodiments of the fluid cassette to measure pressure within a blood processing system, in accordance with embodiments of the present invention.

FIG. 6 shows a process illustrating a method of using the above described cassettes 100 and blood processing system to measure the pressure within a fluid path. First, a technician or system operator may insert the fluid cassette 100 into the blood processing system (Step 610). As mentioned above, the configuration of the cassette 100 is such that, once the cassette 100 is inserted (e.g., upon insertion or after the door 330 is lowered/closed) into the base unit 340, the pressure monitoring device 310 connects to the cassette 100 at the interface 240 and the seal 320 creates a seal between the pressure monitoring device 310 and the interface 240.

Once the operator/technician inserts the cassette 100 and lowers/closes the door 330 (if required), the technician/operator may initiate blood processing (Step 620). As mentioned above, a variety of blood processing procedures and devices (e.g., blood apheresis) may utilize embodiments of the present invention. Once the processing is initiated, whole blood, blood components, or other fluid (e.g., anticoagulant) may begin to flow through the fluid paths 210 within the cassette 100.

As the fluid is passing through the fluid path 210, the pressure monitoring device 310 may then measure the pressure within the fluid path 210 (Step 630). As described above, the pressure monitoring device 310 can measure the pressure within the fluid path 210 based, at least in part, upon the amount the fluid compresses the internal air volume within the cavity 220 or internal volume pathway 520. As the pressure within the fluid path 210 increases, the fluid will further compress the internal volume of air, resulting in the pressure monitoring device 310 measuring a higher pressure. Conversely, if the pressure within the fluid path 210 decreases, the internal volume of air will expand, causing the pressure monitoring device 310 to measure a lower fluid path pressure. If the system is so equipped (e.g., with a microprocessor or other controller), the blood processing system may then increase, decrease, or maintain the fluid flow within the fluid path 210 based upon the pressure measured by the pressure monitoring device 310.

As described above, embodiments of the present invention allow fluid path pressure monitoring to be incorporated into fluid cassettes, which eliminates the manual loading operation required by many of the prior art systems. Additionally, the seals 320 utilized by embodiments of this invention provide a more reliable seal and are far less likely to leak than prior art systems that may utilize tapered luer connections. Embodiments of the present invention also decrease manufacturing costs by simplifying the system, and minimizing the number of additional parts and bonding operations. Furthermore, embodiments of the present invention allow for the automatic loading of the pressure transducer interface with cassette loading and reduce the likelihood that an operator/technician will load the incorrect disposable set.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A fluid cassette for a blood processing system comprising:
   a cassette housing defining a structure of the cassette and having a fluid path at least partially extending through the housing, the fluid path being configured to allow a fluid to pass through the housing; and
   a rigid structure defining a cavity separate from and in fluid communication with the fluid path, the rigid structure having an interface for interfacing with a pressure monitoring device and allowing the pressure monitoring device to measure a pressure within the fluid path, the cavity having a volume of air located between the fluid path and the interface, the cavity including a walled fluid connection pathway and the volume.

2. A fluid cassette according to claim 1, further comprising:
   a bacteriostatic filter located within the rigid structure, the bacteriostatic filter ensuring the fluid path remains sterile.

3. A fluid cassette according to claim 2, wherein the bacteriostatic filter is located at the top of the rigid structure and passes through the interface, the volume of air preventing fluid within the fluid path from contacting the bacteriostatic filter.

4. A fluid cassette according to claim 2, wherein the bacteriostatic filter is a porous plastic plug.

5. A fluid cassette according to claim 2, wherein the bacteriostatic filter is hydrophobic.

6. A fluid cassette according to claim 1, wherein the volume of air within the cavity translates changes of pressure within the fluid path to the pressure monitoring device by compressing and expanding in response to increases and decreases in the pressure within the fluid path.

7. A fluid cassette according to claim 6, wherein an increase in pressure within the fluid path compresses the volume of air, thereby increasing the pressure on the pressure monitoring device.

8. A fluid cassette according to claim 7, wherein the volume of air is large enough such that when the volume of air is fully compressed, the volume of air prevents the fluid within the fluid path from contacting a bacteriostatic filter located within the rigid structure between the fluid path and the pressure monitoring device.

9. A fluid cassette according to claim 1, further comprising a vertical standpipe located within the cavity of the rigid structure.

10. A fluid cassette according to claim 9, further comprising a bacteriostatic filter located within the vertical standpipe.

11. A fluid cassette according to claim 10, wherein the bacteriostatic filter is located at the bottom of the vertical standpipe.

12. A fluid cassette according to claim 10, wherein the vertical standpipe has a standpipe volume, the volume of air not including the standpipe volume.

13. A fluid cassette according to claim 1, wherein the rigid structure is a dome.

14. A fluid cassette according to claim 1, wherein the rigid structure is a pathway.

15. A fluid cassette according to claim 14, wherein the pathway includes the fluid connection pathway and an internal volume pathway, the fluid connection pathway providing fluid communication between the fluid path and the internal volume pathway.

16. A fluid cassette according to claim 15, wherein the interface is located within the internal volume pathway.

17. A fluid cassette according to claim 15, further comprising a bacteriostatic filter located within the internal volume pathway.

18. A fluid cassette according to claim 1, wherein the fluid connection pathway extends from the fluid path to the internal volume and fluidly connects the fluid pathway and the internal volume.

19. A fluid cassette according to claim 1, wherein the cavity intersects the fluid path.

20. A fluid cassette according to claim 1, wherein the cavity extends from the fluid path.

21. A method for monitoring pressure within a fluid cassette for a blood processing system comprising:
   inserting the fluid cassette into the blood processing system, wherein inserting the fluid cassette connects a pressure monitoring device to an interface, the interface located on a rigid structure defining a cavity separate from and in fluid communication with a fluid path located within the fluid cassette, the cavity having a volume of air located between the fluid path and the interface;
   initiating blood processing; and
   measuring the pressure within the fluid path using the pressure monitoring device, the pressure within the fluid path being a function of an amount of compression of the volume of air within the cavity, the cavity including a walled fluid connection pathway and the volume.

22. A method according to claim 21, wherein the fluid cassette includes a bacteriostatic filter located within the rigid structure, the bacteriostatic filter ensuring the fluid path remains sterile.

23. A method according to claim 22, wherein the bacteriostatic filter is located at the top of the rigid structure and passes through the interface, the volume of air preventing fluid within the fluid path from contacting the bacteriostatic filter.

24. A method according to claim 21, wherein the volume of air within the cavity translates changes of pressure within the fluid path to the pressure monitoring device.

25. A method according to claim 21, wherein an increase in pressure within the fluid path compresses the volume of air, thereby increasing the pressure measured by the pressure monitoring device.

26. A method according to claim 21, wherein the volume of air is large enough such that when the volume of air is fully compressed, the volume of air prevents fluid within the fluid path from contacting a bacteriostatic filter located within the rigid structure between the fluid path and the pressure monitoring device.

27. A method according to claim 21, wherein the rigid structure includes a vertical standpipe located within the cavity.

28. A method according to claim 27, wherein the rigid structure includes a bacteriostatic filter located within the vertical standpipe.

29. A method according to claim 28, wherein the bacteriostatic filter is located at the bottom of the vertical standpipe.

30. A method according to claim 27, wherein the vertical standpipe has a standpipe volume, the volume of air not including the standpipe volume.

31. A method according to claim 21, wherein the rigid structure is a dome.

32. A method according to claim 21, wherein the rigid structure is a pathway that includes the fluid connection pathway and an internal volume pathway, the fluid connection pathway providing fluid communication between the fluid path and the internal volume pathway.

33. A method according to claim 32, wherein the interface is located within the internal volume pathway.

34. A pressure monitoring system for use in an apheresis device, the system comprising:
   a fluid cassette having a fluid path therethrough, wherein the fluid path is configured to allow fluid to pass through the cassette, the fluid cassette also having a rigid structure, the rigid structure having an interface and a cavity separate from and in fluid communication with the fluid path, the cavity having a volume of air located between the fluid path and the interface, the cavity including a walled fluid connection pathway and the volume;
   a base unit configured to mate with the fluid cassette; and
   a pressure monitoring device connectable to the interface, the pressure monitoring device measuring the pressure within the fluid path.

35. A pressure monitoring system according to claim 34 wherein the pressure monitoring device measures the pressure within the fluid path based, at least in part, upon an amount of compression of the volume of air.

36. A pressure monitoring system according to claim 34 further comprising a bacteriostatic filter located within the rigid structure and passing through the interface, the bacteriostatic filter ensuring the fluid path remains sterile.

37. A fluid cassette according to claim 34, wherein the volume of air is large enough such that when the volume of air is fully compressed, the volume of air prevents the fluid within the fluid path from contacting a bacteriostatic filter located within the rigid structure between the fluid path and the pressure monitoring device.

38. A fluid cassette according to claim 34, wherein the rigid structure includes a vertical standpipe having a bacteriostatic filter located at the bottom of the vertical standpipe.

39. A fluid cassette according to claim 38, wherein the vertical standpipe has a standpipe volume, the volume of air not including the standpipe volume.

40. A fluid cassette according to claim 34, wherein the rigid structure is a dome.

41. A fluid cassette according to claim 34, wherein the rigid structure is a pathway including the fluid connection pathway and an internal volume pathway, the fluid connection pathway providing fluid communication between the fluid path and the internal volume pathway, the interface being located within the internal volume pathway.

* * * * *